United States Patent
Masuda et al.

[11] Patent Number: 6,063,935
[45] Date of Patent: May 16, 2000

[54] AZETIDINE DERIVATIVE, BIFIDOBACTERIUM DIVISION-PROMOTING COMPOSITION CONTAINING THE SAME, AND A PROCESS FOR PRODUCTION THEREOF

[75] Inventors: Takashi Masuda, Tokyo; Taketoshi Arai, Kanagawa; Kenji Shiojima; Masanori Sasatsu, both of Tokyo; Kazuo Masuda, Kanagawa; Hajime Hamashima; Genichiro Seo, both of Tokyo, all of Japan

[73] Assignee: Toa Pharmaceutical Co., Ltd., Tokyo, Japan

[21] Appl. No.: 09/246,386

[22] Filed: Feb. 9, 1999

[30] Foreign Application Priority Data

Mar. 18, 1998 [JP] Japan .................................. 10-068711

[51] Int. Cl.[7] ........................... C07D 205/00; C12P 17/10
[52] U.S. Cl. .............................................. 548/952; 435/121
[58] Field of Search ........................... 435/121; 514/210; 548/952

[56] References Cited

FOREIGN PATENT DOCUMENTS

| | | |
|---|---|---|
| 2136903 | 12/1972 | France . |
| 67/5790 | 9/1967 | South Africa . |
| 9703693 | 2/1997 | WIPO . |

OTHER PUBLICATIONS

Chemical Abstract, vol. 106, No. 21, May 25, 1987, Abstract No. 174928 Maekawa, et al, "Cultivation of bifidobacterium for manufacture of health foods" –XP002105632.

Chemical Abstract, vol. 106, No. 17, Apr. 27, 1987, Abstract No. 135174, Maekawa, et al, "N–Acyllactams as bifidobacterium growth factors" –XP002105633.

*Primary Examiner*—Deborah C. Lambkin
*Attorney, Agent, or Firm*—McAulay Nissen Goldberg & Kiel, LLP

[57] ABSTRACT

An azetidine derivative is provided which includes 3,3-dihydroxyazetidine represented by Chemical Formula (I) or a salt thereof:

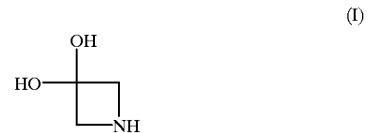

A composition containing the azetidine derivative, and a process for producing the azetidine derivative are also provided. The azetidine derivative is a novel compound, and is useful for promoting bifidobacterium divisional multiplication.

8 Claims, 1 Drawing Sheet

(FIG. 1)
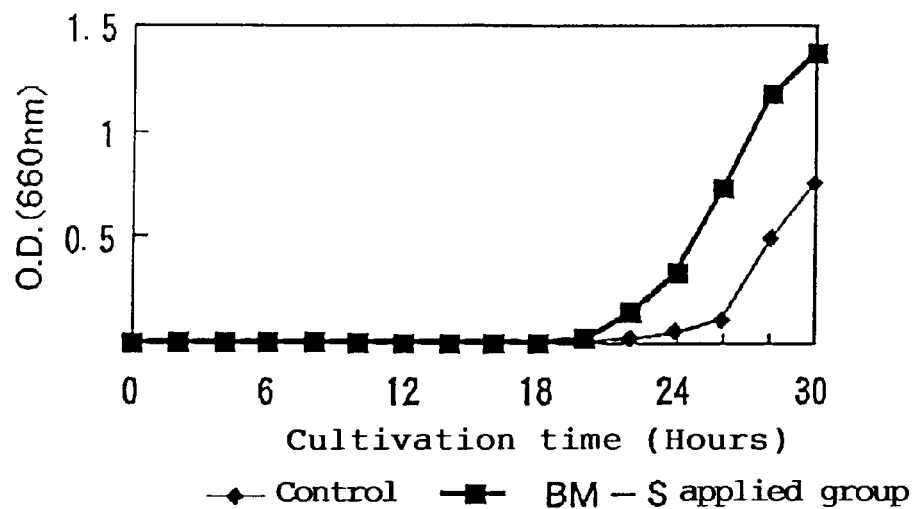

AZETIDINE DERIVATIVE, BIFIDOBACTERIUM DIVISION-PROMOTING COMPOSITION CONTAINING THE SAME, AND A PROCESS FOR PRODUCTION THEREOF

BACKGROUND OF THE INVENTION

1. Field of the Invention

The present invention relates to a novel azetidine derivative, a bifidobacterium division-promoting composition containing the azetidine derivative as an active component, and a process for production thereof.

2. Description of the Related Art

Bifidobacteria are indigenous to healthy living bodies. One gram of fecal matter contains 10,000,000,000 or more bifidobacterium cells. The bifidobacteria produce a varieties of short-chain fatty acids which promote effectively absorption of nutrient sources, water, and electrolytes by the intestinal epithelial cells. Further, the bifidobacteria are known to augment the intestinal immunizing function. The bifidobacteria having such useful properties may decline extremely depending on changes of environmental conditions, external factors, aging, and other factors of the host living body to result in disorder of bowel action. In such a case, the decreased or declined bifidobacteria which are indigenous to the living body need to be activated. The microorganism multiplies by repeating division of cells. An index for the multiplication is a doubling time, which is a time length for one cell generation from a cell division to the next cell division. For example, the average doubling time is 17 minutes for Escherichia coli, 20 minutes for lactic acid bacteria, 30 minutes for Bacillus bacteria, and 120 minutes for yeast. Although quinolone compounds and the like coenzymes are well known to promote the cell division, it is not easy to augment further the inherent multiplication ability of microorganisms. Moreover, the microorganism may lose its growth activity in the case where the microorganism is kept outside its optimum environment conditions: for example, in the case where anaerobic bifidobacterium is kept under aerobic conditions for a long time. In the intestine of a living body also, the bifidobacteria and other bacteria in the intestine content may decline according to disease, environmental change, or aging. Even when the number of the bifidobacterium cells is kept normal, the bowel action may be disordered. In such cases, the multiplication activity of the bifidobacteria is considered to have dropped. To restore the activity, supply of a multiplication-promoting factor for the bifidobacteria can be an effective measure.

Many bifidobacterium multiplication-promoting factors have been reported. Ten and several glycosides typified by oligosaccharides have been commercialized. These bifidobacterium multiplication-promoting substances are characterized mainly by their properties as selective nutrient sources, and are not necessarily sufficient for activation of bifidobacteria having declined multiplication activities.

The known bifidobacterium multiplication factors exert mild actions, and require long time, after administration, in producing the effect of bifidobacterium multiplication, disadvantageously.

Under such circumstances, a medicine is demanded which can be delivered stably to the intestine to promote specifically the multiplication of bifidobacteria in individual bodies with immediate effect.

The inventors of the present invention discovered a novel substance having an estimated molecular weight ranging from 800 to 900 and being capable of promoting the divisional multiplication of various bifidobacteria, including Bifidobacterium longum, B.breve, A.infantis, and B.adolescentis in metabolites formed by Bacillus mesentericus (JP-A-5-344882). The inventors of the present invention found further a novel azetidine derivative of a molecular weight of 90 having bifidobacterium multiplication-promoting activity in a supernatant of a culture medium of Bacillus mesentericus. The inventors of the present invention established a process for production thereof. Thus the present invention has been accomplished.

SUMMARY OF THE INVENTION

The object of the present invention is to provide a compound capable of promoting divisional multiplication of bifidobacteria. Another object of the present invention is to provide a composition containing the compound. A further object of the present invention is to provide a process for producing the compound.

The compound of the present invention is 3,3-dihydroxyazetidine represented by Chemical Formula (I) below, or its salt:

The composition of the present invention contains the azetidine derivative represented by the chemical formula (I) as an effective component.

The process for producing the above compound comprises cultivating a microorganism capable of producing a derivative of an azetidine represented by Chemical Formula (I) to produce the azetidine derivative in the culture medium, and collecting the produced azetidine derivative.

BRIEF DESCRIPTION OF THE INVENTION

FIG. 1 is a graph showing an effect of BM-S on the multiplication of Bifidobacterium longum M101-2.

DETAILED DESCRIPTION OF THE PREFERRED EMBODIMENT

The novel azetidine derivative of the present invention is 3,3-dihydroxyazetidine represented by Chemical Formula (I) below or its salt:

The salt includes addition salts such as hydrochloride, acetate, sodium salts, and potassium salts.

The substance of the present invention can be produced efficiently by a fermentation process with a microorganism. The bacterium strain capable of producing the substance of the present invention includes Bacillus genus bacteria such as Bacillus mesentericus, B.subtilis, and B.natto. Of these, Bacillus mesentericus TO-A (Fermentation Research Institute, Deposition No. FERM P-8934) is the most suitable bacteria strain.

The substance of the present invention may be produced in the manner outlined below. The aforementioned bacterium strain is cultivated under aerobic conditions in a culture containing nutrients usually used for aerobic multiplication of the above bacteria strain. The most suitable culture medium is the one containing meat extract, peptone, and sucrose.

The cultivation can be conducted aerobically. In particular, aeration-agitating cultivation is the most suitable. The cultivation temperature ranges from 30 to 37° C. The pH of the culture medium is preferably neutral. The cultivation time length of 12 hours is sufficient, longer cultivation not contributing the product yield of the intended substance. After the cultivation, the culture supernatant is separated from the microbial mass. From the culture supernatant, the substance of the present invention is separated, and is purified.

The separation and purification can be conducted as described below. Firstly the culture supernatant is separated by centrifugal filtration. The objective substance is allowed to be adsorbed onto a DEAE-Sepharose CL-6B column, and is eluted with a buffer solution to obtain three fractions by reference to the UV absorption spectrum peaks. Of the fractions, the one having the highest bifidobacterium multiplication-promoting activity (hereinafter simply referred to as "activity") is concentrated, and is separated into four sub-fractions. Of the sub-fractions, the one having the highest activity is employed as the active fraction sample. The active fraction is extracted with ether, and the extract solution is concentrated and dried to obtain white needle crystalline matter. This is the substance of the present invention.

The substance of the present invention has no problem in safety, since it is derived from the bacterium strain contained in a living bacterium preparation (Bio-Three: trade name, produced by Toa Yakuhin Kogyo K. K.). The substance is capable of promoting the division of bifidobacterium cells selectively. Therefore, the substance is useful for application fields of medicines, foodstuffs, health foods, functional foods, specified health foods, and the like to relieve disorder of bowel action by improving the bacterial flora in the intestine. In industrial production of the bifidobacteria, the substance is also effective as the multiplication stimulant in activating the seed strain having declined in the growth activity by a long term of storage, or as an additive nutrient for the bifidobacteria in large-scale cultivation.

The substance of the present invention is resistant against heating at 100° C. for 30 minutes. Therefore, the product composition may be preapred in a varieties of states, including powder preparations, granules, and tablets. The product composition may be in a state of a liquid preparation which is effective as food for aged people, or may be added to pellet preparation which is heated in production process.

The substance of the present invention is characterized in the property of promoting the divisional multiplication of bifidobacteria, and is capable of activating bifidobacteria having declined in multiplication activity, which is different from the properties of conventional bifidobacterium multiplication-promoting factors. Experimentally, in cultivation of bifidobacteria having declined in multiplication activity by air exposure, the multiplication activity was restored to the original level by addition of the substance of the present invention in the bifidobacterium multiplication activity measurement conducted by the inventors of the present invention. Such bifidobacterium multiplication-promoting effect is the most important characteristics of the present invention.

EXAMPLE 1

Bacillus mesentericus TO-A (Fermentation Research Institute, Deposition No. FERM P-8934) (hereinafter referred to as "BM") was employed as the bacterium strain. The BM was inoculated to 10 mL of a conventional liquid culture medium (produced by Eiken K. K.) having been sterilized in an autoclave at 121° C. for 1.5 minutes. The BM was cultivated with shaking at 37° C. for 12 hours to obtain seed bacteria. The seed bacteria were inoculated to 500 mL of a BM culture medium (meat extract 1%, peptone 1%, sucrose 1%, sodium chloride 0.5% (pH 7.0)) having been sterilized in an autoclave at 121° C. for 15 minutes and cooled. The bacteria were cultivated with shaking at 37° C. for 24 hours. After the cultivation, the supernatant of the culture medium was separated from the bacterial mass by centrifjgation (5000 rpm, 10 minutes). The supernatant was filtered through a 0.22-$\mu$m membrane filter to eliminate the bacterium cells to obtain about 100 mL of a crude liquid extract (hereinafter referred to as "BM-S").

The obtained BM-S was analyzed by ion-exchange chromatography with a DEAE-Sepharose CL-6B column (column length: 3 cm, column diameter: 20 cm, produced by Pharmacia Co.). The column was washed by 0.02M Tris-HCl solution (pH 7.2). Then adsorbed matter was eluted out with each 100 mL fraction of eluates of 0.1M, 0.2M, 0.3M, and 0.4M NaCl-0.02M Tris-HCl successively. Three peaks were obtained by UV absorption spectrum at 280 nm. The fractions were subjected to bioassay according to bifidobacterium division-promotion activity measurement as described later. Thereby, the fraction FII (hereinafter referred to as "FII") was found to have the activity.

Then 50 mL of FII was concentrated in vacuo to ¹⁄₁₀ volume. One milliliter of the concentrate was charged to a gel filtration column, Sephadex G-25 Superfine (column length: 70 cm, column diameter: 1.6 cm, produced by Pharmacia Co.). The adsorbed matter was eluted with a 0.02 M Tris-HCl solution (pH 7.2) at a flow rate of 30 mL/hour to obtain fractions of 5 mL/tube. Four peaks were found in UV absorption spectrometry. The G-4 fraction was the most active. The G-4 fraction was concentrated to obtain 16 mg of crystalline matter. This is desalted, and purified with a Bond Elut C18 cartridge. The purified matter was analyzed, and found to have the properties below.

(1) Molecular formula: $C_3H_8O_2NCl$ (2) Molecular weight: 125.5 ($M^+$ m/z 90.0618, $C_3H_8O_2N^+$)

(3) Melting point: 145–147° C.

(4) IR absorption spectrum:

Hydroxy: 3250 $cm^{-1}$ and 1040 $cm^{-1}$,

Ammonium: 3000–2000 $cm^{-1}$ and 1640 $cm^{-1}$ (5) 500 MHz $^1H$ NMR:

(Solvent: $CD_3OH$, Internal standard: $(CH_3)_4Si$)

δ: 3.669 (s), 3.308 (ddd, J=1.7 Hz)

(6) 125 MHz $^{13}C$ NMR:

(Solvent: $CD_3OH$, Internal standard: $(CH_3)_4Si$)

δ: 61.06 (methylene carbon), 62.80 (quaternary carbon)

(7) Solubility:

Methanol: Soluble

Chloroform: Hardly soluble

Pyridine: Hardly soluble

Water: Readily soluble (8) State and appearance:

Colorless plate-form crystals

From the above results, the obtained purified product was identified as 3,3-dihydroxyazetidine hydrochloride represented by Formula (I') below.

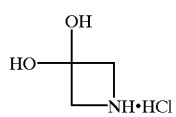

(I')

EXAMPLE 2

The bifidobacterium division-promoting activity was confirmed by the procedure described below. Bifidobacterium longum M101-2 was inoculated to 10 mL of a PY liquid culture medium (tripticase 1%, yeast extract (Difco) 0.5%, a salt solution 4%, L-cysteine 0.05% (pH 7.2)) having been sterilized at 121° C. for 15 minutes. The gas phase was replaced by carbon dioxide gas. Cultivation was conducted at 37° C. for 24 hours to obtain a cultivation solution of B.longum. The cultivated PY culture composition was dispensed aseptically into screw-stopping L-shaped test tubes, and thereto the BM-S obtained in Example 1 was added in an amount of 0.1%. Further thereto, the above B.longum cultivation solution was inoculated such that the B.longum was contained at $1 \times 10^4$ CFU. After the inoculation, the gas phase was replaced by carbon dioxide gas, and the test tubes were tightly stopped. The cultivation was conducted in a Biophoto-Recorder TN-2612 (manufactured by Advantech Co.) by setting the apparatus to measure absorbance at 660 nm every 10 minutes to obtain a multiplication curve of bifidobacterium cells. The control test was conducted by use of a fresh BM culture medium in place of the BM-S.

FIG. 1 shows the resulting multiplication curve, indicating significant shortening of the induction period, and significant improvement of specific multiplication rate in the logarithmic multiplication phase.

The substance of the present invention was subjected to the same measurement for confirmation. The bifidobacterium division-promoting activity was highest at an optimum dilution concentration of $4 \times 10^{-2}$ μg/mL. The results are shown in Table 1.

TABLE 1

The Optimum Concentration of the Substance of the Present Invention

| Tested strain | Concentration of the substance of the present invention | | | | |
|---|---|---|---|---|---|
| | 0 | $4 \times 10$ | $4 \times 10^{-2}$ | $4 \times 10^{-5}$ | $4 \times 10^{-8}$ | $4 \times 10^{-10}$ |
| Bifido-bacterium longum M101-2 | 0.515* | 1.074 | 1.268 | 1.257 | 1.153 | 1,035 |

*Turbidity at 26 hours of cultivation (O.D. = 600 nm)

EXAMPLE 3

The substance of the present invention has activity for the intestinal bacteria as shown below.

By the same manner as in Example 2, the activity was investigated to Bifidobacterium longum, B.adolescentis, B.infantis, B.thermophilum. B.bifidum, B.pseudolongum, B.subtile, B.breve, B.suis, B.globosum, B.pseudocatenulatum, Lactobacillus casei, L.acidophilus, Salmonella typhimurium, Escherichia coli, Pseudomonas aerginosa, Klebsiella oxytoca, and Proteus vulgaris.

The substance of the present invention is confirmed to be active in promotion of division of the respective bifidobacteria, to retard the division multiplication of Escherichia coli, and Pseudomonas aeruginosa, and to be inert to the rest of the bacteria. The results are shown in Table 2 and Table 3.

TABLE 2

Activity of the Substance of the Present Invention on Various Bifidobacteria

| | Substance of the present invention (μg/mL) | |
|---|---|---|
| Tested strain | 0 | $4 \times 10^{-2}$ |
| Bifidobacterium longum M101-2 | 0.515* | 1.268 |
| B.adolescentis A234-4 | 0.518 | 1.002 |
| B.infantis I-10-5 | 0.500 | 0.652 |
| B.thermophilum IV-29 | 0.520 | 0.581 |
| B.bifidum A234-4 | 0.407 | 0.578 |
| B.pseudolongum IV-70 | 0.073 | 0.730 |
| B.subtile IV-110 | 0.502 | 0.635 |
| B.breve I-53-8 | 0.471 | 0.466 |
| B.suis ATCC 27533 | 0.705 | 1.275 |
| B.globosum IV-91 | 0.308 | 0.451 |
| B.pseudocatenulatum BB-110 | 0.533 | 1.010 |

*O.D. = 600 nm

TABLE 3

Activity of the Substance of the Present Invention on Various Intestinal Bacteria

| | Substance of the present invention (μg/mL) | |
|---|---|---|
| Tested strain | 0 | $4 \times 10^{-2}$ |
| Lactobacillus casei NRIC 1042 | 0.420* | 0.420 |
| Lactobacillus acidophilus NRIC 1030 | 0.403 | 0.542 |
| Salmonella typhimurium TA98 | 0.190 | 0.190 |
| Escherichia coli EF72 | 0.408 | 0.250 |
| Pseudomonas aeruginosa PAO | 0.390 | 0.290 |
| Klebsiella oxytoca GIFU 3162 | 0.435 | 0.388 |
| Proteus vulgaris IID 824 | 0.330 | 0.340 |

*O.D. = 600 nm

EXAMPLE 4

The effects of Bacillus genus bacteria on bifidobacterium division-promotion were studied. Filtrates of the culture mediums of the tested Bacillus genus bacteria were prepared in the same manner as the preparation of the crude liquid extract of Bacillus mesentericus TO-A. The respective filtrates were subjected to bioassay. In 14-hour tests, Bacillus mesentericus TO-A, which produces the substance of the present invention, was the most active in bifidobacterium multiplication-promotion. Table 4 shows the results.

TABLE 4

Bifidobacterium Multiplication-Promoting Activity of Culture Filtrate of Bacillus Genus Bacteria

| Tested Strain | O.D. (=600 nm) | Ratio to control |
|---|---|---|
| Control | 0.515* | — |
| Bacillus mesentericus TO-A | 1.144 | 2.22 |
| Bacillus subtilis (natto) A | 1.01 | 1.96 |
| Bacillus subtilis (natto) B | 0.736 | 1.43 |

TABLE 4-continued

Bifidobacterium Multiplication-Promoting Activity
of Culture Filtrate of Bacillus Genus Bacteria

| Tested Strain | O.D. (=600 nm) | Ratio to control |
|---|---|---|
| Bacillus subtilis IAM 1168 | 0.881 | 1.71 |
| Bacillus subtilis IFO 3009 | 1.035 | 2.10 |
| Bacillus subtilis IFO 3034 | 1.067 | 2.07 |
| Bacillus subtilis IFO 13179 | 1.031 | 2.00 |

*O.D. = 600 nm

EXAMPLE 5

A mixture was prepared by mixing 10 g of HM pectin, 1 g of gelatin, 10 g of sucrose, and 0.001 g of the substance of the present invention with sufficient agitation. The mixture was poured into a circular celluloid mold (diameter: 40 mm), and cooled, whereby 500 pieces of jelly food was prepared.

EXAMPLE 6

A mixture was prepared by mixing 50 g of a powdery lactic acid bacterium preparation, 20 g of a powdery butyric acid bacteria preparation, 20 g of a powdery saccharification bacterium preparation, 910 g of PSL (granular mixture of potato starch and lactose), and 0.001 g of the substance of the present invention with sufficient agitation. The mixture is then tableted to prepare 4000 tablets (200 mg per tablet).

The substance of the present invention is capable of promoting divisional multiplication of bifidobacterium. Therefore, the substance is promising not only as a bifidobacterium multiplication factors (bifidobacterium multiplication stimulant, bifidobacterium activator, or the like) outside a living body, but also as orally deliverable activators for bifidobacteria inhabiting in the intestine of humans or animals.

Thereby, the substance of the present invention is capable of relieving the disorder of bowel action such as diarrhea and constipation by improving environment of bacterial flora.

What is claimed is:

1. A process for producing 3,3-dihydroxyazetidine and salts thereof comprising:

cultivating a bacteria of a Bacillus genus capable of producing 3,3-dihydroxyazetidine or salt thereof to produce the 3,3-dihydi oxyazetidine or salt thereof in the culture medium and collecting the produced 3,3-dihydroxyazetidine or salt thereof.

2. The process of claim 1, wherein the Bacillus genus is selected from the group consisting of Bacillus mesentericus, Bacillus subtilis and Bacillus natto.

3. The process of claim 2, wherein the bacteria is Bacillus mesentericus TO-A.

4. The process of claim 1, wherein the cultivating is conducted aerobically.

5. The process of claim 1, wherein the step of collecting comprises separating a culture supernatant from a microbial mass and purifying the 3,3-dihydroxyazetidine or salt thereof from the culture supernatant.

6. The process of claim 5, wherein the step of separating comprises centrifugal filtration.

7. The process of claim 5, wherein the step of purifying comprises adsorption of the 3,3-dihydroxyazetidine or salt thereof to a DEAE-Sepharose column and elution of the 3,3-dihydroxyazetidine or salt thereof from the DEAE-Sepharose column.

8. The process of claim 7, wherein the step of purifying further comprises concentrating the 3,3-dihydroxyazetidine or salt thereof eluted from the DEAE-Sepharose column by extraction with ether followed by drying to form a white needle crystalline product.

* * * * *